United States Patent
McTighe et al.

(10) Patent No.: US 7,323,013 B2
(45) Date of Patent: Jan. 29, 2008

(54) DIFFERENTIAL POROSITY PROSTHETIC HIP SYSTEM

(75) Inventors: Timothy McTighe, Chagrin Falls, OH (US); Ian Murray, Hunt Valley, MD (US); Hugh U. Cameron, Toronto (CA)

(73) Assignee: Encore Medical Asset Corporation, Austin, TX (US)

( * ) Notice: Subject to any disclaimer, the term of this patent is extended or adjusted under 35 U.S.C. 154(b) by 0 days.

(21) Appl. No.: 10/244,149

(22) Filed: Sep. 13, 2002

(65) Prior Publication Data

US 2003/0074079 A1   Apr. 17, 2003

Related U.S. Application Data

(63) Continuation-in-part of application No. 09/505,876, filed on Feb. 17, 2000, now Pat. No. 6,464,728, which is a continuation-in-part of application No. 09/059,698, filed on Apr. 14, 1998, now abandoned.

(60) Provisional application No. 60/372,390, filed on Apr. 12, 2002.

(51) Int. Cl.
*A61F 2/28* (2006.01)
*A61F 2/36* (2006.01)

(52) U.S. Cl. ................ 623/23.5; 623/23.29; 623/23.44

(58) Field of Classification Search .. 623/22.42–22.46, 623/23.21, 23.22, 23.26, 23.29–23.36, 23.44, 623/23.47, 23.5
See application file for complete search history.

(56) References Cited

U.S. PATENT DOCUMENTS

| | | | |
|---|---|---|---|
| 2,719,522 A | 10/1955 | Hudack | |
| 3,067,740 A | 12/1962 | Haboush | |
| 3,102,536 A | 9/1963 | Rose et al. | |
| 3,521,302 A | 7/1970 | Müller | |
| 3,605,123 A | 9/1971 | Hahn | |
| 3,723,995 A | 4/1973 | Baumann | |
| 3,740,769 A | 6/1973 | Haboush | |
| 3,782,373 A | 1/1974 | Smythe | |

(Continued)

FOREIGN PATENT DOCUMENTS

CH   426 096   6/1967

(Continued)

OTHER PUBLICATIONS

Translation of EP 0 720 839 A1.*

*Primary Examiner*—David H. Willse
(74) *Attorney, Agent, or Firm*—Clayton, Howarth & Cannon, P.C.

(57) ABSTRACT

A prosthetic femoral implant for use in a hip joint, as a ball and socket type joint, is disclosed. The implant includes a modular neck having a variety of adjustable positions to adjust the lateral offset and version angle of the femoral implant in relation to the femur. The implant further includes a broad, full collar for providing a compression force increasing the interdigitation between the interface of the bone, implant and cement. The implant also includes a stem having a depression having a roughened porous surface for resisting the increased torsional loads placed on the implant due to the increased lateral offset and version angle. The stem further comprises three distinct zones, each zone having its own roughened surface creating a tripartite differential porosity.

2 Claims, 11 Drawing Sheets

U.S. PATENT DOCUMENTS

| | | |
|---|---|---|
| 3,806,960 A | 4/1974 | Weber |
| 3,808,606 A | 5/1974 | Tronzo |
| 3,820,167 A | 6/1974 | Sivash |
| 3,840,904 A | 10/1974 | Tronzo |
| 3,848,272 A | 11/1974 | Noiles |
| 3,848,273 A | 11/1974 | Frey |
| 3,874,003 A | 4/1975 | Moser et al. |
| 3,894,297 A | 7/1975 | Mittelmeier et al. |
| 3,924,275 A | 12/1975 | Heimke et al. |
| 3,943,576 A | 3/1976 | Sivash |
| 3,965,490 A | 6/1976 | Murray et al. |
| RE28,895 E | 7/1976 | Noiles |
| 3,978,528 A | 9/1976 | Crep |
| 3,987,499 A | 10/1976 | Scharbach et al. |
| 4,012,796 A | 3/1977 | Weisman et al. |
| 4,031,571 A | 6/1977 | Heimke et al. |
| 4,051,559 A | 10/1977 | Pifferi |
| 4,068,324 A | 1/1978 | Townley et al. |
| 4,156,943 A | 6/1979 | Collier |
| 4,206,516 A | 6/1980 | Pilliar |
| 4,304,011 A | 12/1981 | Whelan, III |
| 4,352,212 A | 10/1982 | Greene et al. |
| 4,404,693 A | 9/1983 | Zweymüller |
| 4,430,761 A | 2/1984 | Niederer et al. |
| 4,514,865 A | 5/1985 | Harris |
| 4,530,114 A | 7/1985 | Tepic |
| 4,549,319 A | 10/1985 | Meyer |
| 4,608,052 A | 8/1986 | Van Kampen et al. |
| 4,608,055 A | 8/1986 | Morrey et al. |
| 4,619,659 A | 10/1986 | Witzel |
| 4,666,450 A | 5/1987 | Kenna |
| 4,670,015 A | 6/1987 | Freeman |
| 4,693,724 A | 9/1987 | Rhenter et al. |
| 4,713,076 A | 12/1987 | Draenert |
| 4,714,470 A | 12/1987 | Webb, Jr. et al. |
| 4,718,912 A | 1/1988 | Crowninshield |
| 4,718,916 A | 1/1988 | Morscher |
| 4,728,333 A | 3/1988 | Masse et al. |
| 4,756,711 A | 7/1988 | Mai et al. |
| 4,778,474 A | 10/1988 | Homsy |
| 4,787,907 A | 11/1988 | Carignan |
| 4,790,852 A | 12/1988 | Noiles |
| 4,813,963 A | 3/1989 | Hori et al. |
| 4,822,370 A | 4/1989 | Schelhas |
| 4,828,566 A | 5/1989 | Griss |
| 4,840,630 A | 6/1989 | Kitamura |
| 4,840,631 A | 6/1989 | Mathys |
| 4,846,839 A | 7/1989 | Noiles |
| 4,878,916 A | 11/1989 | Rhenter et al. |
| 4,878,917 A | 11/1989 | Kranz et al. |
| 4,888,023 A | 12/1989 | Averill et al. |
| 4,892,546 A | 1/1990 | Kotz et al. |
| 4,894,064 A | 1/1990 | Imhof |
| 4,908,032 A | 3/1990 | Keller |
| 4,919,670 A | 4/1990 | Dale et al. |
| 4,936,863 A | 6/1990 | Hofmann |
| 4,938,773 A | 7/1990 | Strand |
| 4,944,762 A | 7/1990 | Link et al. |
| 4,950,300 A | 8/1990 | Langlais |
| 4,963,154 A | 10/1990 | Anapliotis et al. |
| 4,963,155 A | 10/1990 | Lazzeri et al. |
| 4,976,738 A | 12/1990 | Frey et al. |
| 4,995,883 A | 2/1991 | Demane et al. |
| 4,997,444 A | 3/1991 | Farling |
| 5,002,578 A | 3/1991 | Luman |
| 5,002,581 A | 3/1991 | Paxson et al. |
| 5,019,108 A | 5/1991 | Bertin et al. |
| 5,030,234 A | 7/1991 | Pappas et al. |
| 5,030,238 A | 7/1991 | Nieder et al. |
| 5,057,101 A | 10/1991 | Dorr et al. |
| 5,062,854 A | 11/1991 | Noble et al. |
| 5,080,685 A | 1/1992 | Bolesky et al. |
| 5,092,898 A | 3/1992 | Bekki et al. |
| 5,092,899 A | 3/1992 | Forte |
| 5,108,452 A | 4/1992 | DeMane et al. |
| 5,116,380 A | 5/1992 | Hewka et al. |
| 5,133,772 A | 7/1992 | Hack et al. |
| 5,147,386 A | 9/1992 | Carignan et al. |
| 5,147,407 A | 9/1992 | Täger |
| 5,152,799 A | 10/1992 | Lyons |
| 5,163,963 A | 11/1992 | Hewka et al. |
| 5,171,324 A | 12/1992 | Campana et al. |
| 5,181,926 A | 1/1993 | Koch et al. |
| 5,197,987 A | 3/1993 | Koch et al. |
| 5,197,988 A | 3/1993 | Spotorno et al. |
| 5,201,882 A | 4/1993 | Paxson |
| D339,634 S | 9/1993 | Hori et al. |
| 5,258,030 A | 11/1993 | Wolfarth et al. |
| 5,258,034 A | 11/1993 | Furlong et al. |
| 5,263,988 A | 11/1993 | Huebner |
| D342,570 S | 12/1993 | Serbousek et al. |
| 5,286,260 A | 2/1994 | Bolesky et al. |
| 5,314,489 A | 5/1994 | Hoffman et al. |
| 5,316,550 A | 5/1994 | Forte |
| 5,326,376 A | 7/1994 | Warner et al. |
| 5,336,268 A | 8/1994 | Rispeter |
| 5,342,366 A | 8/1994 | Whiteside et al. |
| 5,358,525 A | 10/1994 | Fox et al. |
| 5,358,526 A | 10/1994 | Tornier |
| 5,360,446 A | 11/1994 | Kennedy |
| 5,397,359 A | 3/1995 | Mittelmeier et al. |
| 5,443,510 A | 8/1995 | Shetty et al. |
| 5,458,653 A | 10/1995 | Davidson |
| 5,480,451 A | 1/1996 | Grundei et al. |
| 5,480,452 A | 1/1996 | Hofmann et al. |
| 5,653,764 A | 8/1997 | Murphy |
| 5,653,765 A | 8/1997 | McTighe et al. |
| 5,658,349 A | 8/1997 | Brooks et al. |
| 5,702,448 A | 12/1997 | Buechel et al. |
| 5,702,480 A | 12/1997 | Kropf et al. |
| 5,725,594 A | 3/1998 | McTighe et al. |
| 5,725,595 A | 3/1998 | Gustilo |
| 5,876,459 A | 3/1999 | Powell |
| 5,910,171 A | 6/1999 | Kummer et al. |
| 5,935,172 A | 8/1999 | Ochoa et al. |
| 5,954,771 A | 9/1999 | Richelsoph et al. |
| 6,045,556 A | 4/2000 | Cohen |
| 6,083,263 A | 7/2000 | Draenert et al. |
| 6,132,674 A | 10/2000 | Compton et al. |
| 6,165,177 A | 12/2000 | Wilson et al. |
| 6,187,012 B1 | 2/2001 | Masini |
| 6,190,416 B1 | 2/2001 | Choteau et al. |
| 6,190,417 B1 | 2/2001 | Itoman et al. |
| 6,200,350 B1 | 3/2001 | Masini |
| 6,264,699 B1 | 7/2001 | Noiles et al. |
| 6,267,785 B1 | 7/2001 | Masini |
| 6,306,174 B1 | 10/2001 | Gie et al. |
| 6,332,896 B1 | 12/2001 | Hubbard et al. |
| 6,383,225 B2 | 5/2002 | Masini |

FOREIGN PATENT DOCUMENTS

| | | |
|---|---|---|
| DE | 25 58 446 | 7/1976 |
| DE | 26 21 666 | 11/1977 |
| DE | 28 39 661 | 9/1979 |
| DE | 29 33 174 | 4/1980 |
| DE | 31 25 657 | 1/1983 |
| DE | 35 35 158 | 4/1987 |
| DE | 43 20 086 | 12/1994 |
| EP | 0 000 549 | 2/1979 |
| EP | 0 038 897 | 11/1981 |
| EP | 0 050 533 | 4/1982 |
| EP | 0 124 443 | 11/1984 |
| EP | 0 187 903 | 7/1985 |

| | | | | | | |
|---|---|---|---|---|---|---|
| EP | 0 201 407 | 11/1986 | | FR | 2 673 832 | 9/1992 |
| EP | 0 339 530 | 11/1989 | | FR | 2 677 879 | 12/1992 |
| EP | 0 399 920 | 11/1990 | | FR | 2 689 001 | 10/1993 |
| EP | 0 457 222 | 11/1991 | | FR | 2 692 776 | 12/1993 |
| EP | 0 485 311 | 5/1992 | | FR | 2 693 367 | 1/1994 |
| EP | 0 497 079 | 8/1992 | | FR | 2 716 107 A1 * | 8/1995 |
| EP | 0 543 099 | 5/1993 | | GB | 1189325 | 4/1970 |
| EP | 0 720 839 A1 * | 7/1996 | | GB | 1 527 498 | 10/1978 |
| EP | 0 761 182 A2 * | 3/1997 | | GB | 2 126 096 | 3/1984 |
| FR | 2 472 374 | 7/1981 | | JP | 63-59950 A * | 3/1988 |
| FR | 2 574 283 | 6/1986 | | JP | 1-220717 | 9/1989 |
| FR | 2 576 793 | 8/1986 | | JP | 1-300949 | 12/1989 |
| FR | 2 580 171 | 10/1986 | | JP | 10-146352 | 6/1998 |
| FR | 2 606 273 | 11/1986 | | WO | WO 83/02555 | 8/1983 |
| FR | 2 600 526 | 12/1987 | | WO | WO 85/03426 | 8/1985 |
| FR | 2 605 514 | 4/1988 | | WO | WO 91/03992 | 4/1991 |
| FR | 2 616 060 | 12/1988 | | WO | WO 93/03688 | 3/1993 |
| FR | 2 628 628 | 9/1989 | | WO | WO 94/07438 | 4/1994 |
| FR | 2 634 371 | 1/1990 | | WO | WO 96/13230 A1 * | 5/1996 |
| FR | 2 640 497 | 6/1990 | | | | |
| FR | 2 651 674 | 3/1991 | | * cited by examiner | | |

DIFFERENTIAL POROSITY PROSTHETIC HIP SYSTEM

CROSS-REFERENCE TO RELATED APPLICATIONS

This application claims the benefit of U.S. Provisional Application No. 60/372,390, filed Apr. 12, 2002, which is hereby incorporated by reference herein in its entirety, including but not limited to those portions that specifically appear hereinafter, the incorporation by reference being made with the following exception: In the event that any portion of the above-referenced provisional application is inconsistent with this application, this application supercedes said provisional application.

This application is also a continuation-in-part application of U.S. patent application Ser. No. 09/505,876, filed Feb. 17, 2000 now U.S. Pat. No. 6,464,728, entitled "MODULAR NECK FOR FEMUR REPLACEMENT SURGERY," which was a continuation-in-part application of U.S. patent application Ser. No. 09/059,698, filed Apr. 14, 1998 now abandoned, both of which are hereby incorporated by reference herein in their entireties, including but not limited to those portions that specifically appear hereinafter, the incorporation by reference of both applications being made with the following exception: In the event that any portion of the above-referenced applications are inconsistent with this application, this application supercedes said above-referenced applications.

STATEMENT REGARDING FEDERALLY SPONSORED RESEARCH OR DEVELOPMENT

Not Applicable.

BACKGROUND OF THE INVENTION

1. The Field of the Invention.

The present invention relates generally to prosthetic implants, and more particularly, but not necessarily entirely, to a prosthetic hip stem system for enhanced interdigitation between the prosthetic implant and either bone or cement for increasing the torsional stability of the prosthetic implant within the femur.

2. Description of Related Art

It is known in the art to replace the natural hip joint with an artificial hip stem replacement. Numerous artificial implants are available that can be installed to replace the natural hip joint with an artificial ball and socket combination. The medullary canal may be opened using a reamer to create a passage through the medullary canal in the upper end of the femur where a hip stem may be implanted. A stem or femoral component of an artificial implant is inserted into the reamed portion of the medullary canal in a secure, seated position. Typically, femoral implants include a neck member that extends outward and away from the stem and terminates in a spherical knob for insertion into the acetabulum of the hip in rotational contact therewith about the three major orthogonal axes.

There are two major systems to secure the femoral component of the implant within the medullary canal of the femur. The first system utilizes the natural tendencies of the bone and allows the bone to grow into porous sections of the implant without the aid of cement. The cementless system requires the removal of all cancellous bone and uses bone ingrowth to form a tight, secure fit between the implant and the bone, which maintains the implant within the bone. This system was first introduced nearly forty years ago and has become the preferred method of installation due in part to the strength of the connection between the implant and the bone.

The second system utilizes bone cement to maintain the implant within the bone. The use of cement requires the removal of bone tissue while leaving a layer of cancellous bone tissue to anchor the implant with the aid of cement. This process was used extensively during the 1980's and is still used today on a more limited basis.

Both systems may be advantageous depending upon a patient's needs. For example, recovery from an operation using the cementless system takes an average of about three months before the patient may return to any activity so that the bone may be permitted to grow into the pores of the implant, which results in a connection that has the potential to endure in the patient for a long period of time. This system is recommended for patients who lead active lives and is typically used in relatively young patients. Conversely, the cemented system results in a decrease in pain compared to the cementless system and an increase in joint mobility. However, the interface between the bone, the cement and the implant may not last as long as the cementless system. Therefore, the cemented system is typically used in less active, older patients.

It is a fairly common occurrence for femoral implants to loosen from the bone or cement over time due in part to the high stresses placed on the hip joint. Attempts have been made in the prior art to increase the efficiency of the bond between the implant and either bone or cement, such that the loosening of the implant from the bone or cement over time is decreased. One way of improving the adhesion of the stem of the implant to the bone or cement is found in U.S. Pat. No. 4,430,761 (granted Feb. 14, 1984 to Niederer et al.). Niederer et al. discloses a femoral prosthesis having a plurality of parallel grooves formed on the shank or stem of the implant to improve adhesion of the shank in a prepared bone cavity.

However, the system disclosed by Niederer et al. is disadvantageous for those situations where, for one reason or another, the implant must be removed and replaced. The location of the grooves at the distal end of the femoral prosthesis is disadvantageous because during the removal process in order to completely loosen the implant from the bone the surgeon must have adequate access to those portions of the implant where bone ingrowth has occurred. With grooves located on the distal end of the implant, the surgeon does not have adequate access to loosen that portion of the implant from the bone and the implant is, therefore, very difficult to remove.

There are many other systems known in the prior art for improving the adhesion between the implant and the bone or cement, such as that disclosed in U.S. Pat. No. 4,828,566 (granted on May 9, 1989 to Griss). This patent reference discloses a shank or stem having a recess in the proximal medial region with a U-shaped wire mesh disposed in said recess for providing an ingrowth of bone tissue and an absorption of shear micro movements between the bone and the implant. However, this system is disadvantageous because torsional forces may still be exerted on the implant, which may loosen the implant over time.

U.S. Pat. No. 3,965,490 (granted Jun. 29, 1976 to Murray et al.) discloses a femoral implant having one or more shallow teardrop-shaped depressions disposed in the flat sides of the curved proximal portion of the stem. These teardrop depressions provide extra surfaces and directional configuration, which facilitates retention within the medullary canal of the femur. However, this system is disadvantageous because there is a tendency for the implant to loosen from the cement due in part because the surface of the implant is smooth and does not provide a surface for interdigitation with the cement.

It is noteworthy that none of the prior art known to applicants provides a femoral implant having a tripartite differential porosity where the distal portion of the stem comprises the smoothest section, the proximal portion of the stem comprises a section rougher than the distal portion, and the teardrop recess comprises the roughest section of the stem and is rougher than the proximal portion. Applicants have discovered that it is advantageous for femoral implants used as part of a total hip replacement system to mimic the natural biomechanics of the hip through increasing the lateral offset, which is accomplished by increasing the length of the neck portion of the implant, which thereby increases the torsional load on the femoral implant. Applicants have further discovered that the use of differential roughness on the proximal portion, distal portion and the recessed portion of the stem opposes and resists the increased torsional load placed on the femoral implant. There is a long felt but unmet need, for a tripartite differential porosity femoral implant which has the ability to resist the increased torsional loads created by the larger lateral offset. This is accomplished by using a recessed section that may be advantageously located on both the posterior and anterior sides of the prosthesis, resulting in an increase in torsional stability in the connection between the stem and the femur. The increase in stability is due, at least in part, to the recessed section located at the posterior and anterior sides of the prosthesis, but not on the medial or lateral sides of the prosthesis, such that abrasion wear is not increased on the medial side.

The prior art is thus characterized by several disadvantages that are addressed by the present invention. The present invention minimizes, and in some aspects eliminates, the above-mentioned failures, and other problems, by utilizing the methods and structural features described herein.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the appended claims.

BRIEF DESCRIPTION OF THE DRAWINGS

The features and advantages of the invention will become apparent from a consideration of the subsequent detailed description presented in connection with the accompanying drawings in which.

DETAILED DESCRIPTION OF THE INVENTION

Figure 1:
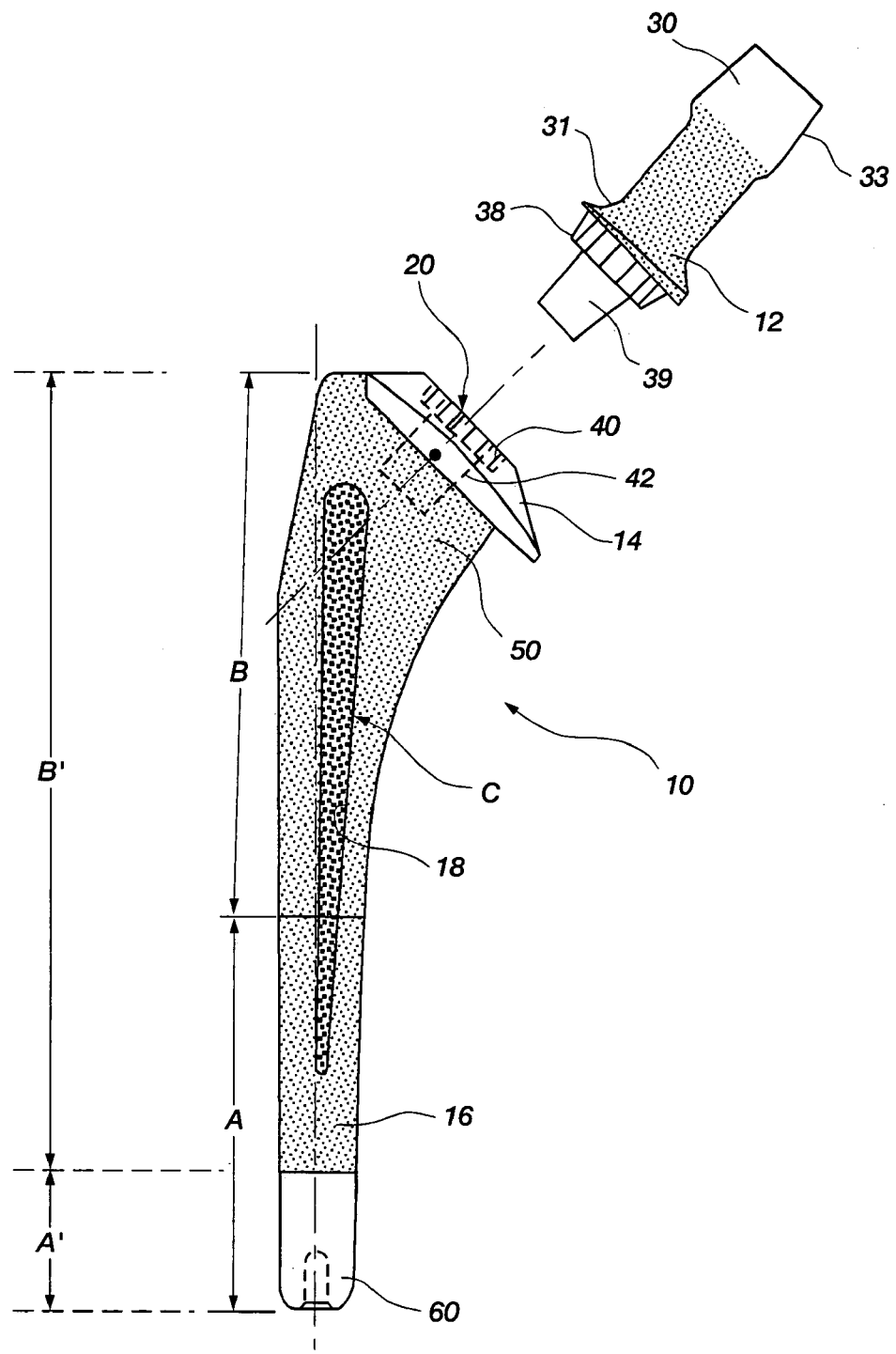
FIG. 1 is a side view of a prosthetic femoral implant, specifically illustrating a collar portion, a modular neck portion, and a stem portion having a plurality of surficial zones, each zone having a roughness, made in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Before the present device and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

Figure 8:
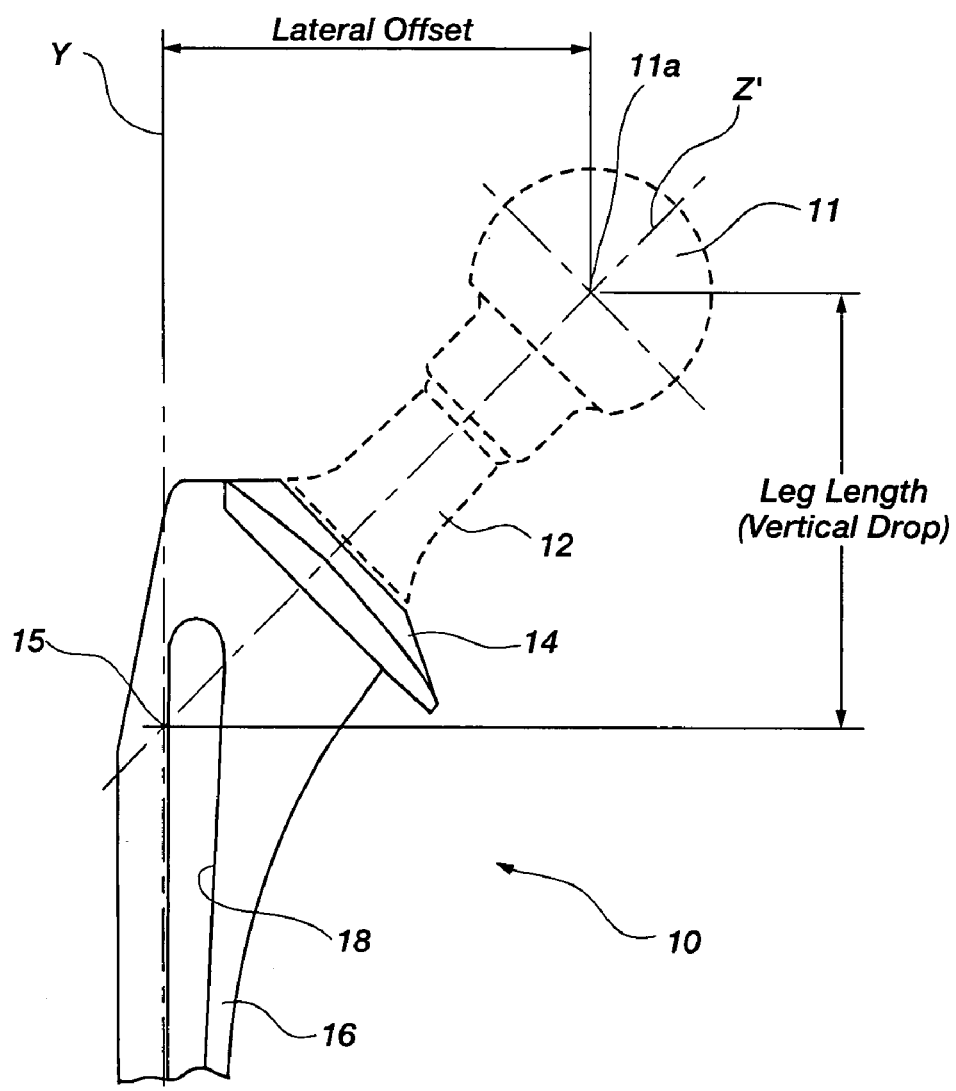
FIG. 8 is an enlarged side view of the prosthetic implant illustrating the lateral offset and the vertical drop of a head and neck combination.

Referring generally to FIG. 8, a "focal point," referred to as item 15, may be defined as a point of convergence of two axes, namely a long axis, represented by the line Y, of a femoral stem portion 16 of a prosthetic implant 10, and a neck axis, represented by the line Z', of the prosthetic implant 10. The phrase "lateral offset" refers to the horizontal distance relative to a patient in a standing position from the center of the pelvis to the center of the femoral canal in the natural hip joint. In the prosthetic implant 10, "lateral offset" refers to the horizontal distance between a center 11a of a ball or femoral head portion 11 of the implant 10 and the long axis Y of the femoral stem portion 16 of the implant 10. The phrase "vertical drop" refers to the vertical distance between the center 11a of the head portion 11 and the focal point 15.

Figure 6:
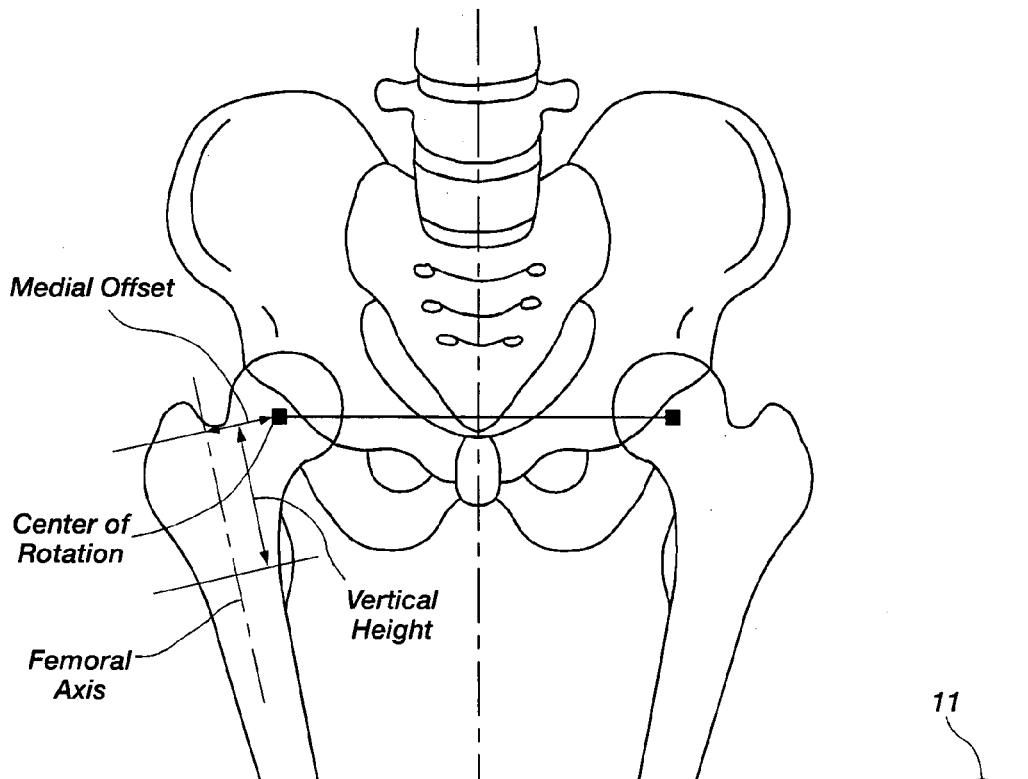
FIG. 6 is a schematic view of a human pelvis illustrating the natural placement of the femur within the hip joint, and the naturally occurring lateral offset of the femur within the hip joint.

Designers of hip stem prostheses may choose to increase the lateral offset by increasing or decreasing the distance between a center of the ball or femoral head of the implant and the mid-line, or long axis, of the femur in order to aid in the restoration of the biomechanics of the natural hip joint, as illustrated in FIG. 6. An increased lateral offset operates to increase the torsional forces that are exerted on the femoral implant, and such forces become applied to the cement-implant interface between the implant and the medullary canal of the femur. There is therefore, in cases of an increased lateral offset, an increased need for torsional stability to prevent the implant from loosening from the bone or cement.

Applicants have also discovered that torsional forces may be more effectively opposed by applying a type of differential porosity to the surface of a femoral implant, to resist the torsional forces. Applicants have further discovered that the femoral implant may be more effectively tuned or adjusted after implantation of the femoral stem into the medullary canal of the femur, by selectively increasing or decreasing the lateral offset, and the version angle of the neck, using a modular neck component. In some instances, it is advantageous to adjust the lateral offset and the version angle simultaneously.

Figure 7:
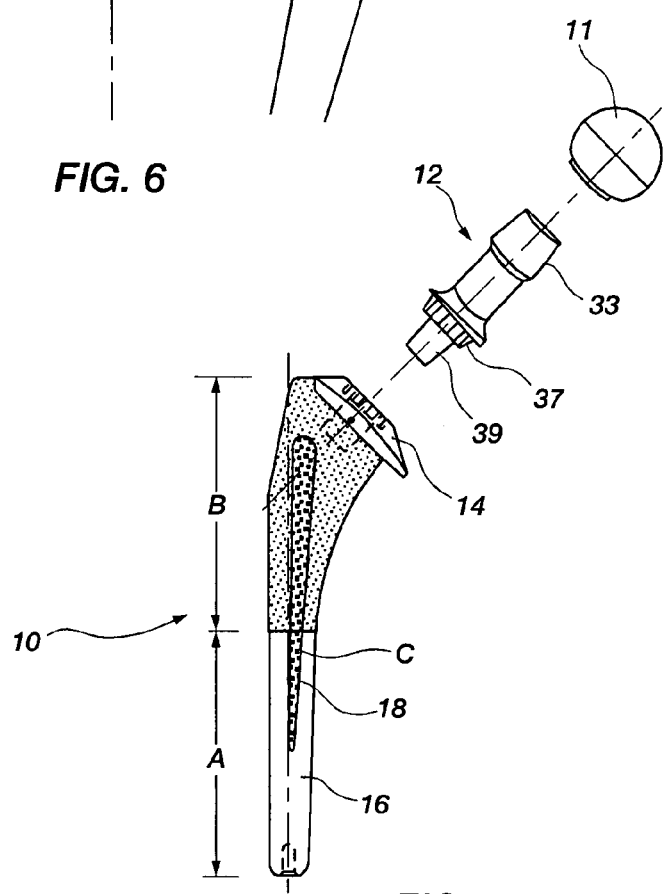
FIG. 7 is an exploded side view of the prosthetic implant illustrating the head portion, the modular neck portion and the stem portion of the implant, made in accordance with the principles of the present invention.

Referring now to FIGS. 1 and 7, there is shown a side view of a femoral prosthetic implant designated generally at 10, illustrated with a medial side of the implant 10 facing downward in FIG. 1 and to the right in FIG. 7. The femoral prosthetic implant 10 comprises a substantially spherical femoral head 11 (illustrated best in FIGS. 4 and 7), which may be attached to a modular indexable neck portion 12 for use as the ball portion of a ball and socket joint, a collar portion 14, a stem portion 16 comprising a proximal stem region 50 and a distal stem region 60, and a teardrop-shaped depression 18 located between the proximal stem region 50 and the distal stem region 60. The above components may be manufactured from titanium for cementless stem applications and from cobalt chrome molybdenum alloy in cemented stem applications for interfacing with cement and for providing less risk of fretting and corrosion at the modular stem neck junction. It should be noted that other material may be used that are presently known, or which may become known, in the art for manufacturing the above components, which can be readily determined by one of skill in the art. Each of the above components will be more particularly described below in relation to FIGS. 1, 4 and 7.

As used herein, the term "fixation material" may be defined as bone that may grow into the implant, bone cement that may interdigitate with the implant, or any other substance that one of skill in the art may use for securing the implant to the bone to inhibit torsional loads that is presently known, or which may become known in the future, in the art without departing from the scope of the present invention.

Figure 4:
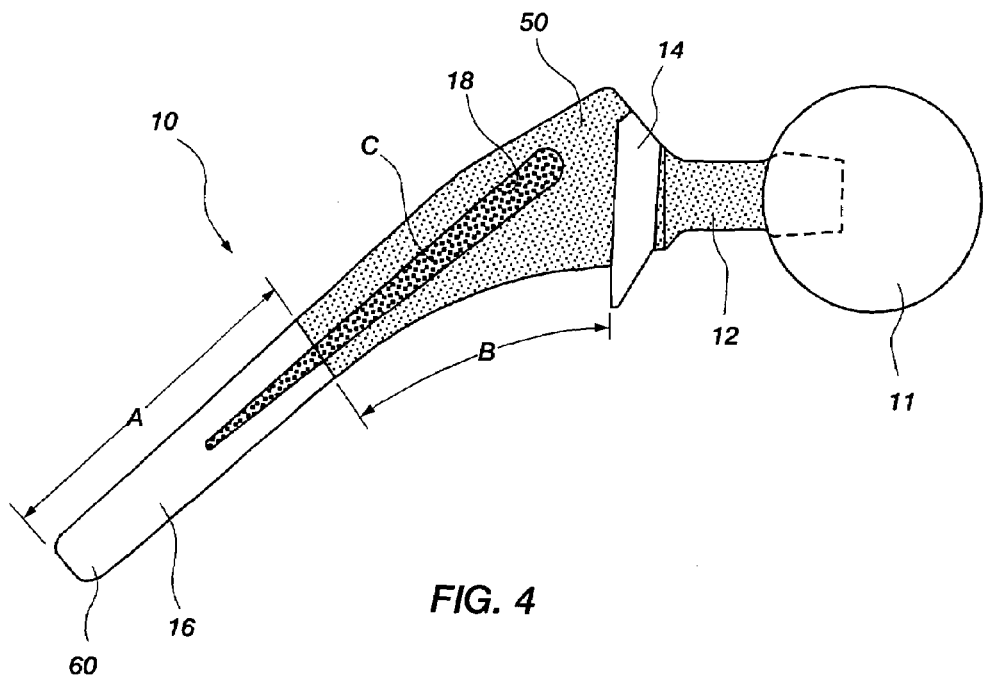
FIG. 4 is a side view of a prosthetic femoral implant, similar to FIG. 1, illustrating a femoral head portion of the prosthetic femoral implant attached to the modular neck portion and the stem portion, made in accordance with the principles of the present invention.

The present invention is directed to utilize a prosthetic hip having an increased lateral offset between the spherical ball portion 11, sometimes referred to herein as a head portion (illustrated in FIG. 4), of the prosthetic implant 10 and the shaft of the patient's femur (illustrated best in FIG. 6). It should be noted that any suitable head portion 11, which may be substantially spherical in shape, either presently known in the art, or which may become known in the future, may be utilized by the present invention as the ball portion of the ball and socket joint. The head portion 11 may be configured for articulating with an articulation surface, which articulation surface may be an acetabular cup or other surface used to assemble the socket portion of a ball and socket joint. The head portion 11 may be modular and attached to the neck portion 12 by a taper lock as illustrated in FIG. 4, or the head portion 11 may alternatively be integral with the neck portion 12 (not illustrated in the figures).

Figure 2:
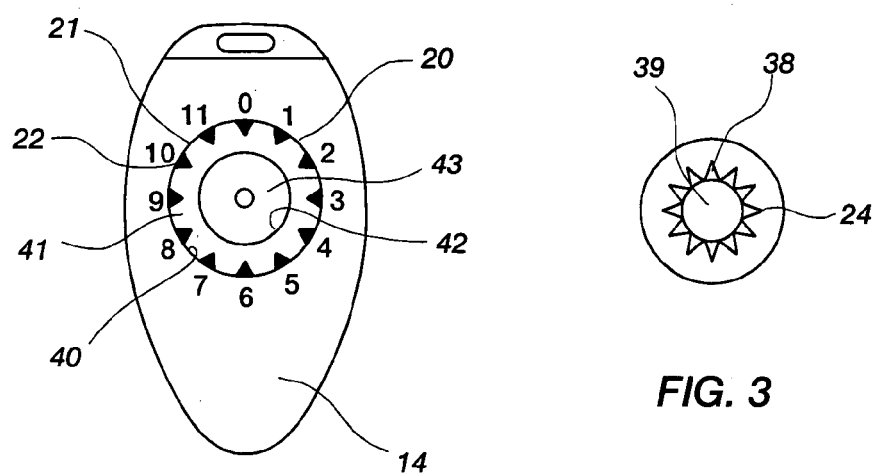
FIG. 2 is a top view of the prosthetic femoral implant of FIG. 1, specifically illustrating a top surface of the collar portion, with the modular neck portion removed, having a cavity formed therein, made in accordance with the principles of the present invention.

The present invention may also utilize a modular neck portion 12 to create the lateral offset required to aid in restoring the natural biomechanics of the joint. The natural biomechanics of the hip joint is demonstrated in FIG. 6. Referring back to FIG. 1, neck portion 12 may be adjusted by a surgeon after the prosthetic implant 10 has been implanted within the femur, by changing the orientation of the neck portion 12 to any one of a plurality of differing positions as illustrated in FIG. 2. Although there are twelve such positions shown in FIG. 2, it is to be understood that the implant 10 may be designed to accommodate more or fewer than twelve such selectable positions.

Neck portion 12 may be replaced with various sizes of necks 12, for example by a longer neck or shorter neck than that shown in the figures, with the size of the neck depending upon the need of the patient. The neck size may be determined by the surgeon at the time of surgery. The length of the neck portion 12 may be configured and dimensioned to correspond with the increased need for lateral offset. Some exemplary lengths of the modular neck portion 12 include 32 mm, 35 mm, and 38 mm. It should be noted that any size neck portion 12 may be used to increase the lateral offset and one of skill in the art could modify the length of the neck portion 12 to match the varying needs and anatomies of each individual patient.

The neck portion 12 comprises a proximal end 30 and a distal end 31. The proximal end 30 comprises a smooth surface 32 that may have a slightly tapered outer edge 33 such that the proximal end 30 may matingly engage a matching opening located within the head portion 11 such that the head portion may be secured to the neck portion 12 as illustrated in FIG. 4. It should be noted that one of skill in the art may modify the shape of the tapered outer edge 33 to increase or decrease the taper angle or to be of any shape, including no taper, presently known, or which may become known, in the art to secure the neck portion 12 to the head portion 11. The above structural features may be referred to herein as a means for attaching the indexable neck portion to the head portion. As noted previously, the head portion 11 may alternatively be integrally attached to the neck portion 12 without departing from the scope of the present invention.

Figures 5, 5A:
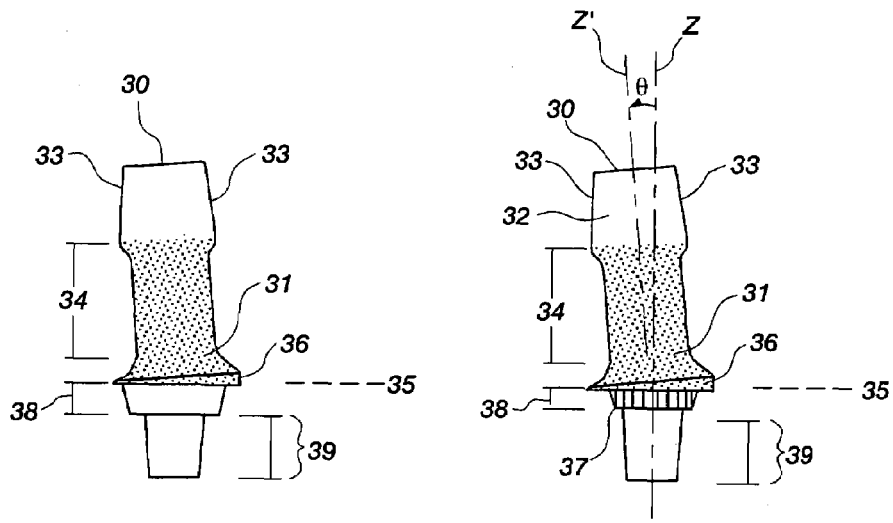
FIG. 5 is a side view of one embodiment of the modular neck portion made in accordance with the principles of the present invention.
FIG. 5A is a side view of an alternative embodiment of the modular neck portion made in accordance with the principles of the present invention.

As illustrated particularly in FIG. 5, a long axis of the neck portion 12, referred to herein as the reference axis Z, may be defined as being normal to a plane 35 of the base of the neck portion 12. An angle θ, also referred to herein as an anteversion angle θ, is also illustrated in FIG. 5, and may be defined as the angle between the reference axis Z and an anteverted axis, also referred to herein as the neck axis, represented by the line Z'. Thus, the angle θ of the neck portion 12 permits the head portion 11 to be located either farther anteriorly, or farther posteriorly within the hip joint. Exemplary anteversion angles θ may be between the range of about zero and about twelve degrees. It should be noted that one of skill in the art could modify the anteversion angle θ without departing from the scope of the present invention such that the anteversion angle θ could be greater than twelve degrees, depending upon the need of the patient and the desired result.

The neck portion 12 further comprises a shaft 34 separating the proximal end 30 from the distal end 31. The neck portion 12 comprises a raised portion 36 located near the base of the shaft 34 on the distal end 31, positioned at an angle with respect to the neck axis Z' creating the anteversion of the neck portion 12 as illustrated most clearly in FIGS. 5 and 5A, and discussed above. It should be noted that one of skill in the art may modify the angle of the raised portion 36 to increase or decrease the anteversion angle θ or may reposition the raised portion 36 to any position presently known, or which may become known, in the art to create an anteversion in the neck portion 12. It should further be noted that one of skill in the art could modify the current invention without departing from the scope of the present invention so as to eliminate the raised portion 36 completely, and simply angle the shaft 34 of the neck portion 12 to the desired anteversion angle θ.

The surface of the shaft 34 and the distal end 31 of the neck portion 12 may contain a roughness as illustrated in FIGS. 5 and 5A. It should be noted that one of skill in the art may modify the surface of the neck portion 12 such that the roughness may be increased to an even rougher surface, or such that the neck portion 12 may be smooth, instead of rough, without departing from the scope of the present invention.

The distal end 31 of the modular neck portion 12 may comprise an indexable portion extending therefrom. The distal end 31 may also comprise a first tapered portion 38 disposed thereon, sometimes referred to herein as a first insert, and may further comprise a second tapered portion 39, sometimes referred to herein as a second insert, extending below and being disposed on the first tapered portion 38. This combination of tapers may be referred to herein as a double taper. One embodiment of the first tapered portion 38 includes a geared section 21 illustrated in FIG. 5 comprising a plurality of male gears 37 for matingly engaging a corresponding female geared section 21 of the stem portion 16. It should be noted that the male gears 37 may be tapered as it is a part of the first tapered portion 38. The male gears 37 function to act in concert with the female geared section 21 of the stem portion 16 permitting the modular neck portion 12 to be indexed in a plurality of positions and orientations, thus altering the angle of anteversion with respect to the stem portion 16 and permitting the surgeon the ability to fine tune and adjust the modular neck portion 12 such that the stress points may be altered or shifted.

An alternative embodiment of the first tapered portion 38 comprises a taper without gears and may be fashioned as illustrated in FIG. 5A. It should be noted that the first tapered portion 38 may be modified by one of skill in the art to be of any length, either larger or smaller than illustrated in FIGS. 5 and 5A, presently known, or which may become known in the future, in the art for securing the neck portion 12 to the stem portion 16, and may further be modified to increase or decrease the angle of taper without departing from the scope of the present invention.

The second tapered portion 39 extends below the first tapered portion 38 and may be between the range of about two to about five times the length of the first tapered portion 38. It should be noted that the length of the second tapered portion 39 may be modified, as illustrated in FIGS. 5 and 5A, by one of skill in the art to provide a taper that does not bottom out and provides a secure connection between the neck portion 12 and the stem portion 16. For example, FIG. 5 illustrates one embodiment of the second tapered portion 39 as being longer than an alternative embodiment of the second tapered section 39 illustrated in FIG. 5A.

The second tapered portion 39 functions to provide a primary self-locking taper for locking and securing the neck portion 12 to the stem portion 16. Whereas, the first tapered portion 38 functions as a secondary locking taper to secure the neck portion 12 to the stem portion 16, and may act as an emergency backup to maintain the connection between the neck portion 12 and a cavity 20 such that the stem portion 16 does not separate from the rest of the prosthetic implant 10, should the primary locking taper fail for any number of reasons.

During a hip replacement surgery, it is common for a surgeon to experience at least the following two problematic scenarios. The first scenario relates to the patient's anatomy where the stem portion 16 cannot be surgically placed in an upright orientation with respect to the medullary canal of the femur (not shown), causing a skewed orientation of the implant 10. The second scenario occurs when the surgical technique of the surgeon results in less than perfect orientation of the stem portion 16 within the medullary canal of the femur (not illustrated). In either scenario the result is the same, the orientation of the stem portion 16 is not aligned with the shaft of the femur causing pain and discomfort to the patient as well as reducing the longevity of the implant, which will loosen over time due to the differing forces placed on the implant. The present invention permits the surgeon during surgery to fine tune and adjust the orientation of the stem with the shaft of the femur by replacing one neck portion 12 with another to create the desired lateral offset and create the desired orientation for each individual patient. The ability to permit positioning of the modular indexable neck portion 12 independent of the stem portion 16, by varying the version angle and the offset angle (and hence the offset itself) simultaneously in order to fine tune the implant 10 to the patient's needs, whether to match the original biomechanics of the hip joint or to produce an altered position that is different from the original biomechanics of the patient, causes altered stress points to become applied to the cement-implant interface. There is usually more stress imposed in comparison to many prior hip stem designs, thus precipitating a need for increased torsional stability and resistance. One solution is explained below in connection with the differential porosity, or roughness, of the stem portion 16.

The stem portion 16 may be designed such that it may aid in the restoration of the natural joint mechanics and for allowing the surgeon a final opportunity to correct for malpositioning of implants 10 due to surgical technique and bone deformity. The proximal stem 50 may contain collar portion 14 configured with a cavity 20 where a self-locking taper and a positive indexing mechanism may be employed to ensure that the proper head, length, version and offsets may be obtained. This unique design may feature provides a plurality of self-locking positions providing several combinations of neck length version and offset for closely aiding in the restoration of the natural hip joint mechanics. This innovative design provides the surgeon with the opportunity to intervene at the last possible surgical moment and fine tune the hip joint mechanics without disruption of the implant-cement-bone interface. In addition, the design of the stem portion 16 provides for increased opportunity to surgically intervene for certain post-operative complications, for example, component malposition, leg length discrepancy, dislocations and replacement of bearing surfaces, with minimal disruption of the interfaces of the bone.

FIG. 2 illustrates a top view of the collar portion 14 having a cavity 20 formed therein. Within the cavity 20 may be a first sidewall 40 defining a first portion 41 having twelve different positions denoted by numerals 0-11 situated in a similar position as a standard clock. The differing orientations may be established by a female geared section 21, which permits the neck portion 12 to have differing version angles with respect to the stem portion 16, which may be adjusted by removing the neck portion 12 from the cavity 20 and rotating the neck portion 12 to the desired orientation creating the desired version angle. The female geared section 21 of the cavity 20 may be configured and dimensioned with slight protrusions 22 extending inwardly into the cavity 20 from the first sidewall 40 creating a plurality of female gears to matingly engage the male gears 37 of the modular neck portion 12 for adjusting the orientation of said modular neck portion 12.

Figure 3:
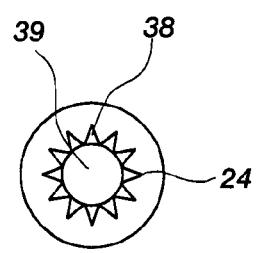
FIG. 3 is a bottom view of the modular neck portion, which has an indexable portion shaped to correspond with the cavity formed in the top of the collar, made in accordance with the principles of the present invention.

FIG. 3 illustrates the corresponding bottom portion of the modular neck portion 12 having male gears 37 with mating protrusions 24 for mating with the female gear section and may be spaced between protrusions 22 such that the two arrays of protrusions mate with one another forming a matching fit. Mating protrusions 24 function similarly to protrusions 22 in that the mating protrusions 24 permit the modular neck portion 12 to be adjusted into twelve differing version angles. It should be noted that the number of protrusions and gears may be modified by one of skill in the art to include more or less than twelve differing positions in which the neck may be oriented such that differing version angles may be achieved. For example, by removing two protrusions 22 or female gears from the cavity 20 and removing the same number of corresponding mating protrusions 24 or male gears 37 from the first tapered portion 38, ten different positions may be achieved instead of twelve. The same relationship holds true for adding protrusions 22 or female gears and mating protrusions 24 or male gears 37.

A second sidewall 42 within the cavity 20 defines a second portion 43 that may be tapered to match the taper of the second tapered portion 39 of the modular neck portion 12 such that a secure lock may be achieved between the stem portion 16 and the modular neck portion 12. The taper of the second portion 43 may be of the self-locking type and provides for the primary fixation of the stem portion 16 to the neck portion 12. The depth of the second portion 43 may be dimensioned such that the second portion 43 may be deep enough to avoid "bottoming out" of the taper, ensuring that the self-locking taper may occur. Thus, the first tapered portion 38 of the modular neck portion 12 may be configured for matingly engaging the first portion 41 of the cavity 20 forming a secondary lock or fixation, and the second tapered portion 39 of the modular neck may be configured for matingly engaging the second portion 43 of the cavity 20 forming a primary lock or fixation of the self-locking type. The above structural features may be referred to herein as a means for attaching the indexable neck portion to the stem portion.

The collar portion 14 may be disposed on the stem portion 16 by extending from the proximal region 50 of the stem portion 16 in a medial, anterior and posterior direction creating a broad, full collar portion 14. The broad, full collar (i.e. more than just a medial collar) aids in compression of the bone cement into the differential surface porosities (described in more detail below), during implantation to provide a more consistent cement mantel interface by creating a force for counter-pressure. The force created by the full collar portion 14 provides for optimal/complete interdigitation of the cement with the bone as well as with the implant. Therefore, the collar portion 14 functions to force cement into the medullary canal of the femur as well as into the porous depressions on the surface of the prosthetic implant. Additionally, when the stem portion 16 of the prosthetic implant 10 is seated within the medullary canal of the femur the collar portion 14 functions as a cap to cover the medullary canal such that wear debris generated from the prosthetic implant may be prevented from migrating into the medullary canal.

Below the collar portion 14 extends the stem portion 16, which may be configured and dimensioned to be surgically located within the medullary canal of the femur. As referred to previously and as illustrated in FIG. 4, the stem portion 16 comprises a proximal region 50, a distal region 60 and a depression 18 located between the proximal region 50 and the distal region 60. The depression 18 may be defined by a boundary with the boundary defining the overall shape of the depression. The stem portion 16 may be divided into multiple separate and distinct zones, each zone having its own unique surface porosity or roughness, thereby creating a differential porosity or differential roughness. FIGS. 1 and 4 illustrate three zones of differing porosity or roughness, zone A, zone B and zone C. It is to be understand that more or fewer than three zones of porosity or roughness may be used. The first zone, designated as A, comprises the distal stem 60 and may be configured and dimensioned with either a very slight porous surface or with no porous surface at all creating a smooth surface. The second zone, designated as B, substantially comprises the proximal stem 50 and may be configured and dimensioned with a porous surface that is rougher than zone A. The third zone, designated as C, comprises a teardrop-shaped depression 18 that may be configured and dimensioned with an even rougher porous surface than zone B and provides increased torsional stability for the implant 10. Therefore, zone A has the smoothest surface, zone B has a rougher surface than zone A and zone C has the roughest surface of all three zones, creating a tripartite differential porosity or roughness.

The rougher surfaces of zones B and C provide surfaces to which either the bone may interdigitate with and grow into more effectively, or to which the bone cement may adhere to more effectively to thereby secure the implant 10 to the medullary canal of the femur. The smooth surface of zone A provides a surface that bone and cement will not adhere to as effectively, such that the distal portion 60 of the stem portion 16 will be more easily removable from the medullary canal of the femur, should removal of the implant 10 become necessary. The benefit of the tripartite differential porosity or roughness is an increased torsional stability in the connection between the stem portion 16 and the femur, at the posterior and anterior sides of the prosthesis, but not on the medial or lateral sides of the prosthesis, such that abrasion wear is not increased on the medial side. Such a differential roughness may sometimes be referred to herein as a means for resisting torsional loads.

The distal portion 60 of the stem portion 16 or zone A may have a finish that has a polished finish between the range of 2-15 RA. The proximal portion 50 of the stem portion 16 or zone B may have a rougher satin finish between the range of 15-30 RA. The depression 18 may have an enhanced satin polish that may be between the range of 30-80 RA, which is rougher than the proximal portion's 50 satin finish.

It will be appreciated that zones A, B and C may each be modified, such that the area of the implant 10 that each zone includes may be increased or decreased. For example, FIG. 1 illustrates the zones A, B and C, with zone A being roughly the same length on the stem as zone B. However, zone A may be shortened to include the area covered by zone A', thus decreasing the area of zone A while increasing the area of zone B to include the area covered by zone B'. It is evident from FIG. 1, that one of skill in the art may modify the area of each zone to include a larger or smaller area and thus proportionally increasing or decreasing the amount of surficial roughness present in a given zone.

The stem portion 16 may include roughness depressions 18 of any suitable shape. For example, the stem portion 16 may include a single teardrop-shaped depression 18, or the stem portion 16 may alternatively comprise two opposing teardrop-shaped depressions 18. Teardrop-shaped depressions 18 may be located on the anterior and posterior portions of the stem portion 16 and may extend from a proximal stem region 50 into a distal stem region 60. The depressions 18 may be located on the anterior and posterior portions and aid in securing the stem portion 16 to the implant-bone cement interface, and which functions to oppose the torsional forces experienced in the hip joint. Additionally, the depression(s) 18 located on either the anterior portion, the posterior portion or on both portions of the stem portion 16 may be a single depression or may be a series of multiple depressions effectuating a single depression 18.

The porosity or roughness of the depression 18 may fill the entire depression 18 or may fill only a portion of the depression 18, depending upon the desired result. FIGS. 1 and 4 illustrate the depression 18 having a boundary defining the depression 18 or recessed surface, in which the boundary of the depression 18 is the same as the boundary of the porosity or roughness. The surface of the depression 18 provides for increased interdigitation between the implant 10 and the cement or bone and causes the implant 10 to have an increased ability to resist the increased torsional loads placed on the implant 10 responsive to the increase in lateral offset and version angle, both of which create an increased need for torsional resistance. It should be noted that the size of the teardrop-shaped depression 18 may be modified to be of any suitable size and accomplish the same results. It should be further noted that while the shape of the depression(s) 18 has been illustrated as teardrop-shaped, one of skill in the art may modify the shape of the depression 18 to be of any shape presently known, or which may become known, in the art to inhibit torsional forces.

As stated previously, the surface of the stem portion 16 may contain a roughness as illustrated in FIGS. 1 and 4. The roughness may be comprised of a material such as beads that have been bead blasted onto the surface of the stem portion 16 such that the surface area of the stem portion 16 may be increased for increasing the interdigitation between the bone, the implant 10 and the bone cement such that a more secure fixation of the implant 10 to the bone may be achieved. It should be noted that the method of applying the surficial roughness to the stem portion 16 may be modified by one of skill in the art using a method presently known, or which may become known in the future, in the art for adding a surficial roughness to the stem portion 16. Additionally, the material, design and shape used to create the roughness may be modified by one of skill in the art using any suitable material, design and shape presently known, or which may become known, in the art for increasing the surface area and interdigitation of the stem portion 16.

Applying the differential surficial roughness described above is an advantageous feature of the present invention. Advantageously, it is a feature of the present invention to have a different surficial roughness located within the depression 18 as opposed to the surficial roughness of the proximal stem region 50 and the distal stem region 60 because as the surface of the stem portion 16 increases in roughness there is a corresponding increase in surface area, which increased surface area causes greater contact between the bone cement or other fixation material and the stem portion 16. Increased contact between the fixation material and the stem portion 16 results in increased strength, stability and resistance to withdrawal forces such that the implant may be securely fastened to the bone.

Applying the above surface area principles it will be noted that zone A has the smoothest surface and has less surface area than both zone B and zone C. The reason for the decreased surface area is in large part due to the fact that it is difficult to remove the distal stem 60 from the femoral bone once the stem portion 16 has been implanted into the femur and that difficulty is increased when the surface area of the distal stem 60 is increased. As noted above, as the surface area of the distal stem 60 increases, the strength of the bond between the bone fixation material and the distal stem 60 also increases and becomes extremely difficult to remove the implant 10 from the bone should it become necessary to remove the implant 10 for revision surgery. Removal becomes extremely difficult because there is no technique available, barring drastic resection, for the surgeon to get instrumentation into the distal portion of the femur that permits the surgeon to sufficiently loosen and remove the implant 10.

Zone B, comprising the proximal stem 50, has similar problems as the distal stem 60 with respect to removal of the stem portion 16. However, the surficial roughness and hence the surface area of the proximal stem 50 may be increased because the proximal stem 50 is more readily accessible to the surgeon as the surgeon may use instrumentation to pry the stem and ultimately the implant 10 from the bone. In this case, the increased roughness in zone B is advantageous because it increases the bonding strength, which results in greater stabilization of the implant 10 within the femur.

Zone C, comprising the depression 18, may contain the greatest roughness and results in the greatest surface area of all three zones. Therefore, there is a large amount of interdigitation between the fixation material and the depression 18, which results in great bonding strength. Additionally, because the depression or depressions are located on the anterior and posterior portions of the stem portion 16 the increased roughness and surface area of the depressions 18 operate to oppose the increased torsional forces that are experienced as the natural biomechanics of the femur are simulated by increasing the lateral offset and version angle of the modular neck portion 12. Further, the increased bonding strength does not prevent removal of the stem portion 16 from the medullary canal of the femur because of the tear-drop shape of the depression 18, with the majority of the depression 18 being located in the proximal stem region 50 and the remainder of the depression 18 being located in the distal stem region 60. Therefore, the differential roughness of the present invention advantageously utilizes unique, novel design features that increase resistance to torsional forces.

Further, the depression 18, while increasing the bonding strength and hence resisting torsional forces, may be used as a part of a mechanism to break the bond between the fixation material and the implant 10. For example, an instrument (not shown in the figures) may be used to initially uncover the proximal most portion of the depression 18. The instrument may be used to break the bond by following the depression 18, which acts as a channel or guide for the instrument, loosening the implant 10 from the fixation material.

Referring now to FIG. 8, wherein an enlarged side view of the proximal portion of the femoral prosthetic implant 10 with the neck portion 12 and the head portion 11 secured to the stem portion 16. Specifically, the lateral offset between a center 11a of the head portion 11 and the mid-line or longitudinal axis, represented by the line Y, of the femoral implant 10 is illustrated along with the corresponding vertical drop associated with the size of the modular neck portion 12 and head portion 11 to be used. The vertical drop may be determined as the vertical distance between the center 11a of the head portion 11 of the implant 10 and the intersection of the longitudinal axis Y and a neck axis Z' at the focal point 15. The neck axis Z' runs through the center 11a of the head portion 11 and extends through the neck portion 12. As the size of the neck portion 12 and the size of the head portion are changed, the lateral offset as well as the vertical drop will also change accordingly. For example, as the neck portion 12 increases in size, the lateral offset will necessarily increase as the center 11a of the head portion 11 is positioned farther away from the longitudinal axis Y, thus changing the vertical drop as well. Conversely, as the neck portion 12 decreases in size, the center 11a of the head portion 11 is brought closer to the longitudinal axis Y, reducing the lateral offset as well as the vertical drop.

Referring now to FIGS. 9-14, wherein specific examples of how the size of the femoral head portion 11 and size of the neck portion 12 affect the lateral offset and vertical drop of the implant 10. FIGS. 9-14 are intended as illustrative examples only, and are not intended to be limiting of the scope of the present invention.

Figure 9:
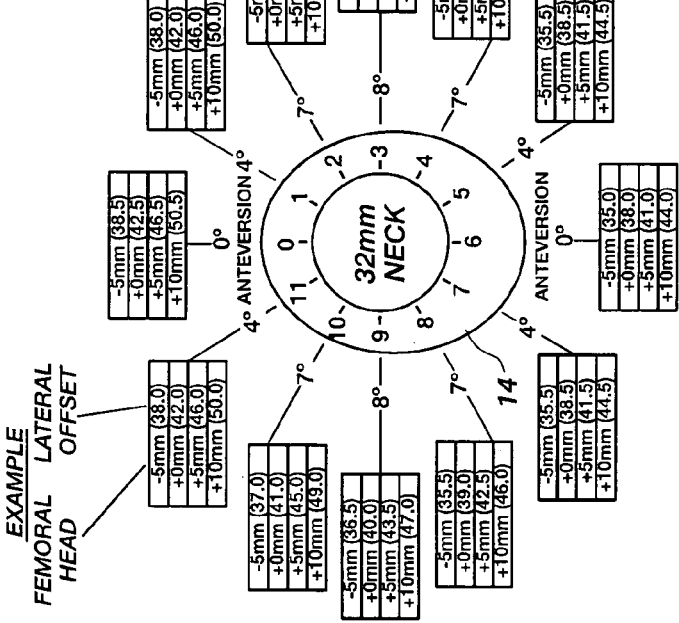
FIGS. 9 through 11 are illustrations representing several examples of the lateral offset and the vertical drop as illustrated in FIG. 8 using an anteversion angle of eight degrees in the modular neck portion.
Figure 10:
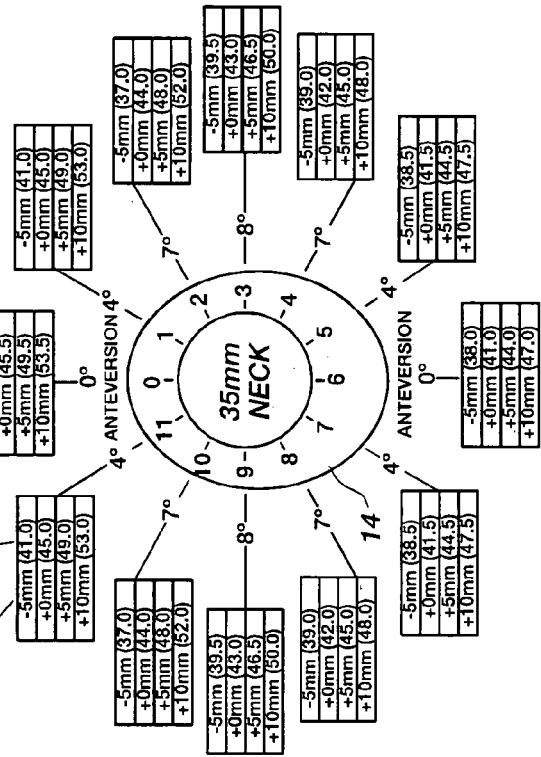
Figure 11:
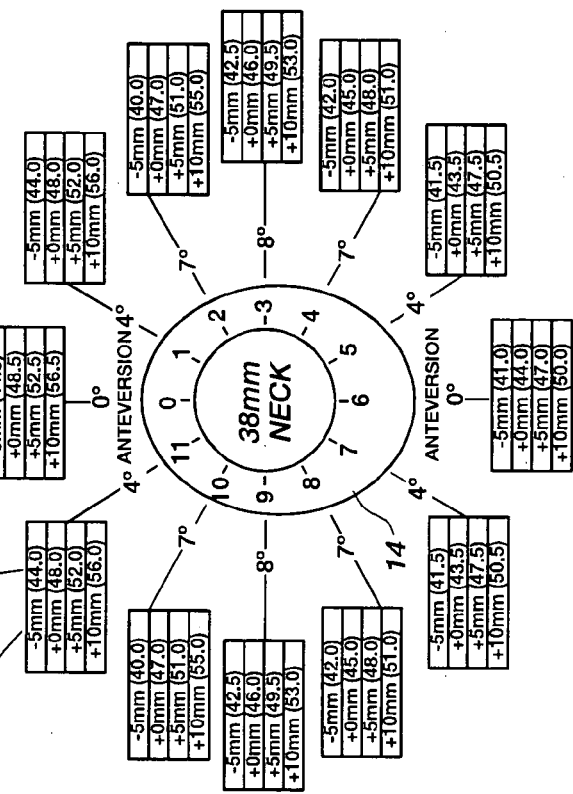
Figure 12:
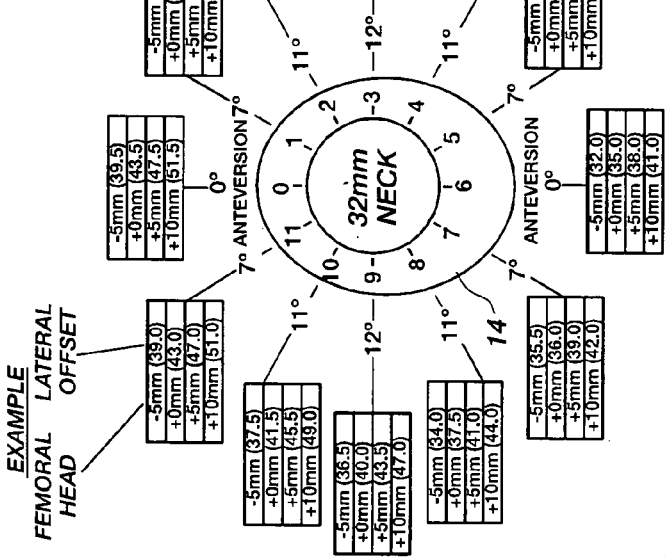
FIGS. 12 through 14 are illustrations representing several examples of the lateral offset and the vertical drop as illustrated in FIG. 8 using an anteversion angle of twelve degrees in the modular neck portion.
Figure 13:
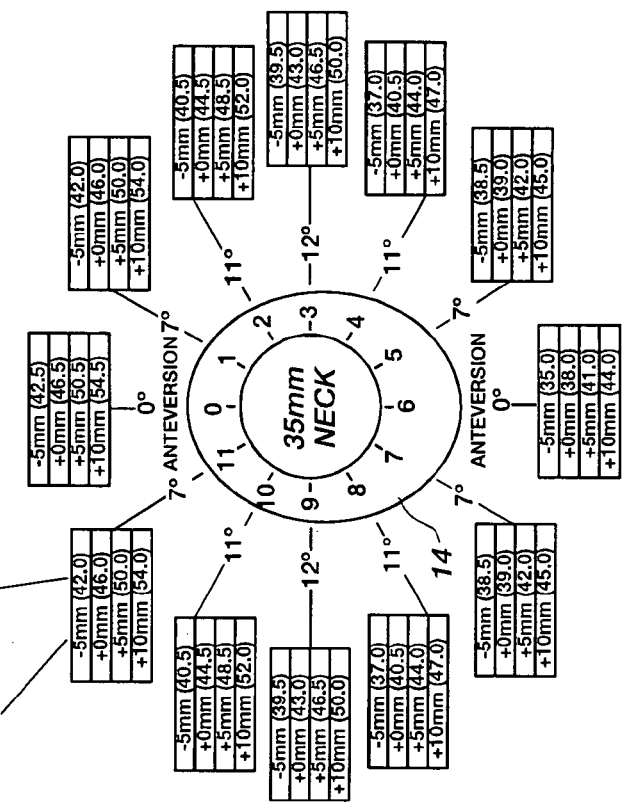
Figure 14:
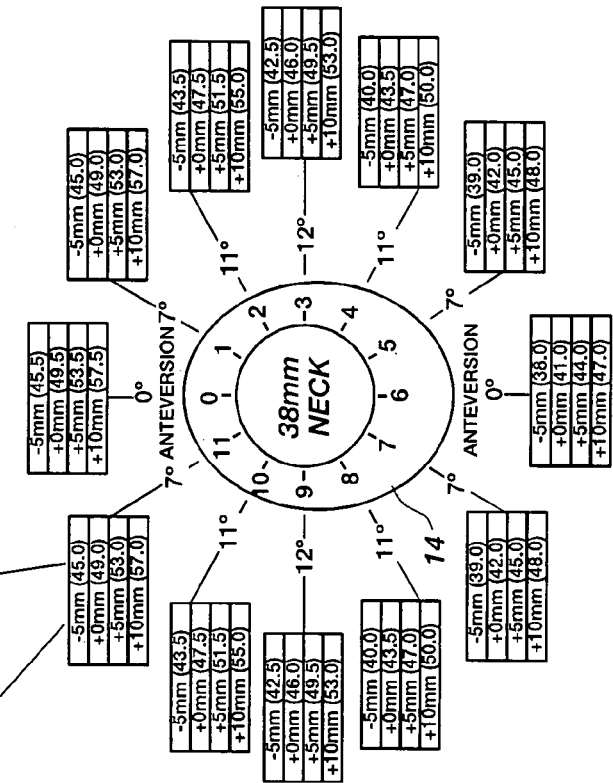

It should be noted that FIGS. 9-11 use an eight degree anteversion angle θ in the neck portion 12, while FIGS. 12-14 use a twelve degree anteversion angle θ in the neck portion 12. It should further be noted that FIG. 9 utilizes a 32 mm neck portion 12, FIG. 10 utilizes a 35 mm neck portion 12, and FIG. 11 utilizes a 38 mm neck portion 12. The same sizes of neck portions 12 are also used in the illustrations of FIGS. 12-14.

It will be appreciated that one exemplary demonstration of how to use the illustrations of FIGS. 9-14, may be applicable to each of the illustrations of FIGS. 9-14. For example, FIG. 9 utilizes a neck portion 12 having an anteversion angle θ equal to eight degrees, and the neck portion 12 is 32 mm in length. Referring specifically to the circular chart and lateral offset in FIG. 9, the collar portion 14 is illustrated as having twelve positions numbered 0-11. Position number 11 will now be used to demonstrate how the charts may be read. When the neck portion 12 is located in position number 11, the neck portion 12 has a four degree anteversion angle θ. Further, as labeled, the small chart associated with position number 11 represents the femoral head size and the associated lateral offset. As the size of the femoral head portion 11 is increased or decreased, as noted above in relation to FIG. 8, the lateral offset may also be increased or decreased as noted in the chart. Thus, a +5 mm femoral head will have a corresponding lateral offset of 46 mm. Referring now to the leg length vertical drop chart of FIG. 9, the +5 mm femoral head located in position number 11 will also correspond to a 41 mm vertical drop. Therefore, as demonstrated above, as the length of the neck portion 12 or the size of the femoral head changes, the corresponding lateral offset and associated vertical drop will also change accordingly. It should be noted that the remaining position numbers may be referred and interpreted in like manner as position number 11 demonstrated above.

Those having ordinary skill in the relevant art will appreciate the advantages provided by the above-described features of the present invention. Current surgical technique requires the surgeon to expose the proximal portion of the femur and the acetabular portion of the hip joint, and perform an osteotomy of the proximal portion of the femur. Such a resection of the proximal femur causes the bone to bleed. The surgical devices of the prior art utilize a prosthetic implant having a neck that is integral with the stem. When using an integral neck, the surgeon is required to implant the acetabular cup and its component parts into the acetabulum and then attach the femoral head to the acetabular cup prior to implanting the femoral component of the prosthesis into the exposed femoral canal. Implanting the acetabular components typically takes approximately thirty minutes for a surgeon to complete. Thus, while the surgeon is preparing the acetabulum and securing the acetabular cup and other components therein, the resected proximal femur remains exposed and continues to bleed. The result is often an unnecessary loss of blood between the range of 200-400 cc in volume.

Conversely, the advantageous features of the present invention described above permit the surgeon to avoid unnecessary bleeding in original hip replacement surgeries and aid the surgeon in subsequent revision surgeries if needed. For example, the modularity of the neck portion 12 of the present invention permits the surgeon to resect the proximal femur, expose and otherwise prepare the femoral canal and then implant the stem portion 16 of the prosthetic implant 10 promptly into the femoral canal without having to wait for the surgeon to implant the acetabular cup and its component parts into the acetabulum, which reduces excessive bleeding in the femur. The implantation of the stem portion 16 into the femoral canal acts similarly to a plug being inserted into a hole to stop a leak, and thereby reduces excessive bleeding in the femur. Thereafter, the surgeon may proceed with the implantation of the acetabular components without unnecessary blood loss in the femur. Finally, the surgeon may attach the modular neck portion 12 to the implanted components and finish the remainder of the surgery.

Another advantageous feature of the present invention may be realized during the unfortunate occurrence of a revision surgery to replace damaged components or for any other reason a revision surgery may be necessary. For example, when a prosthetic device having an integral neck has been surgically implanted on a previous occasion, and it becomes necessary for the surgeon to replace the acetabular cup on the socket side of the joint by implanting a bone graft, there is a high risk of damaging the femoral component of the prosthetic implant 10. This is because the head portion 11 and the neck portion 12 are connected to the acetabular cup in the acetabulum and may get in the way during removal, making it difficult to remove the acetabular cup without damaging the femoral component. In this circumstance, the only other option for the surgeon, besides potentially damaging other components, is to try to avoid the integral neck. However, such avoidance compromises the quality of the surgical procedure.

Once again the modularity of the neck portion 12 of the present invention advantageously permits the surgeon to detach the modular neck portion 12 from the remainder of the implant 10. At that point, the surgeon may expose the needed area to perform the revision surgery and then reattach the modular neck portion 12 without the need to remove the stem portion 16 from the femur and posing a risk of damaging the femur or the stem portion 16.

An additional advantageous feature of the modular neck portion 12 of the present invention may be realized in a revision surgery when the previously implanted stem and neck are chrome cobalt or other metallic material, but the prosthetic femoral head is ceramic. It is a contra-indication to take a ceramic femoral head off and then reattach it again to the neck in the original circumferential grip friction-pressure fit, because the ceramic can split or crack at the tapered connection by the inherent stress riser that exists in a friction fit involving a circumferential grip. Therefore, using the integral necks of the prior art causes the surgeon to replace the entire femoral component in order to avoid refitting and possibly splitting the ceramic head, which requires further resection of the femur. However, using the present invention, the surgeon can simply replace the entire head and neck combination without having to remove the stem portion 16 by simply detaching the neck 12 from the stem 16. Therefore, the contra-indication of ceramic is avoided without removing the stem portion 16 of the implant 10 from the femur, which eliminates unnecessary bone resection.

In accordance with the features and combinations described above, a useful method of attaching a prosthetic femoral implant to a patient's femur includes the steps of:

(a) creating a passage into the medullary canal of the femur by removing at least a portion of the cancellous bone;

(b) pouring an amount of bone cement into the medullary canal;

(c) inserting a femoral prosthetic implant having a modular neck, a full collar, and stem, said stem comprising a proximal portion, a distal portion and a teardrop-shaped depression, each portion of the stem being separate and having distinct porosity creating a tripartite differential porosity surface, into the bone cement; and (d) providing a compression force on the collar of the femoral prosthetic implant for shaping the bone cement into a consistent cement mantle and for creating increased interdigitation between the bone, bone cement, and implant interface.

It should be noted that the present invention and the principles taught herein may be used for implanting a prosthetic device either with or without bone cement without departing from the scope of the invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A prosthetic device for implantation into a bone comprising:

a longitudinal stem portion configured and dimensioned for insertion into a canal formed within the bone, said stem portion having a proximal region, a distal region, and a single anterior depression and a single posterior depression configured to provide resistance to torsional loads;

wherein the proximal region, the distal region each have a different surficial roughness than the single anterior depression and the single posterior depression for increasing the surface area of the stem portion and increasing the interdigitation between the stem portion and a fixation material such that torsional loads are further resisted;

wherein the distal region is completely smooth and is of the same unchanging texture, except for a distal end portion of the single anterior depression and the single posterior depression.

2. A prosthetic device for implantation into a bone comprising:

a longitudinal stem portion configured and dimensioned for insertion into a canal formed within the bone, said stem portion having a proximal region, a distal region, and at least one depression formed between the proximal region and the distal region, said at least one depression configured to provide resistance to torsional loads;

wherein the proximal region, the distal region and the at least one depression each have a different surficial roughness for increasing the surface area of the stem portion and increasing the interdigitation between the stem portion and a fixation material such that torsional loads are further resisted;

wherein the at least one depression comprises the roughest surficial roughness of all the regions of the stem portion and the distal region comprises a smooth surficial roughness that is the smoothest of all the regions of the stem portion;

wherein the smooth surficial roughness of the distal region comprises substantially the entire distal end of said stem portion.

* * * * *